United States Patent [19]

Gorski et al.

[11] Patent Number: 4,884,558
[45] Date of Patent: Dec. 5, 1989

[54] LARYNGOSCOPE ASSEMBLY INCLUDING DISPOSABLE PROTECTIVE ENCLOSURE

[75] Inventors: Lawrence J. Gorski; Nancy G. Gorski, both of Camarillo, Calif.

[73] Assignee: Gorsk, Inc., Camarillo, Calif.

[21] Appl. No.: 123,204

[22] Filed: Nov. 20, 1987

[51] Int. Cl.⁴ .............................................. A61B 1/06
[52] U.S. Cl. ...................................................... 128/11
[58] Field of Search ................... 128/11, 12, 909, 4, 128/6, 17, 79, 132 R; 206/363, 364, 368, 438, 829; 433/116; 2/168; D24/17

[56] References Cited

U.S. PATENT DOCUMENTS

| | | | |
|---|---|---|---|
| D. 242,346 | 11/1976 | Baumann | D24/17 |
| D. 242,397 | 11/1976 | Baumann | D24/17 |
| D. 242,398 | 11/1976 | Baumann | D24/17 |
| D. 253,009 | 9/1979 | Okamoto | 128/132 R |
| 2,073,137 | 3/1937 | Bimrose | 433/116 |
| 2,989,755 | 6/1961 | O'Brien et al. | 2/168 |
| 3,426,749 | 2/1969 | Jephcott | 128/11 |
| 4,064,564 | 12/1977 | Casey | 2/168 |
| 4,492,220 | 1/1985 | Hayes | 128/17 |
| 4,570,614 | 2/1986 | Baumann | 128/11 |
| 4,646,722 | 3/1987 | Silverstein et al. | 128/4 |
| 4,728,290 | 3/1988 | Eisner et al. | 433/116 |

Primary Examiner—Edward M. Coven
Assistant Examiner—Mark S. Graham
Attorney, Agent, or Firm—Edward W. Osann, Jr.

[57] ABSTRACT

A laryngoscope assembly comprising a handle, a blade, and a connector fitting joining the two; and a disposable, impervious, elastic safety enclosure which is light permeable and adapted to be stretched longitudinally and diametrically over said assembly to maintain its sanitary integrity.

8 Claims, 1 Drawing Sheet

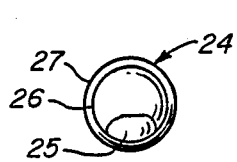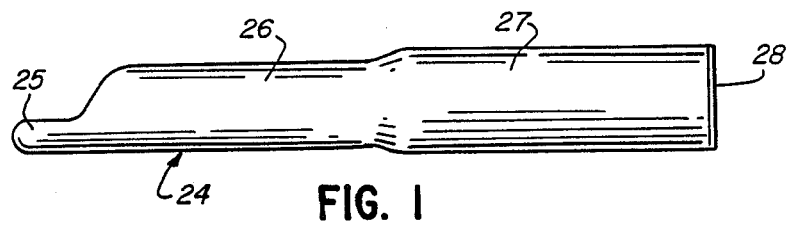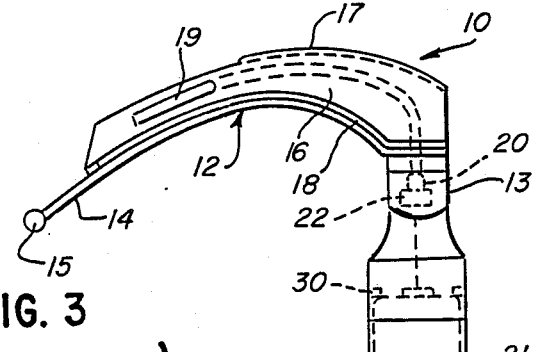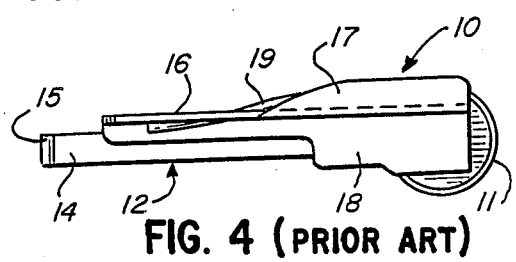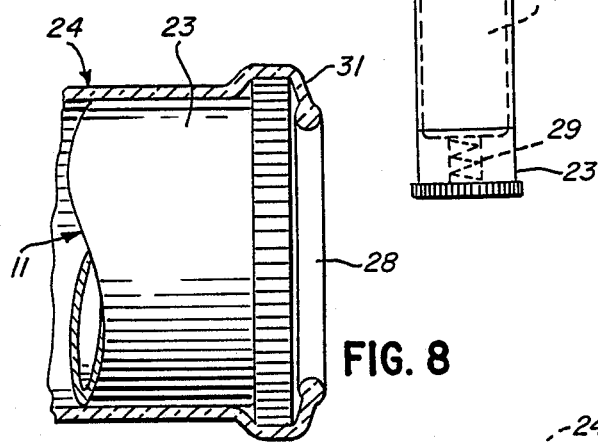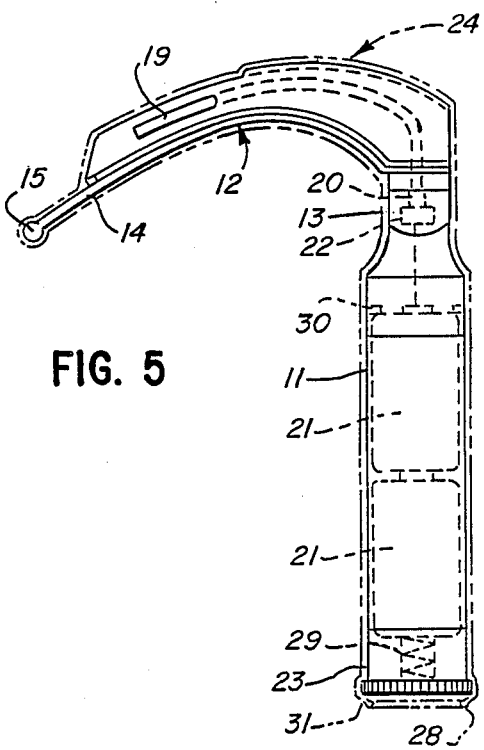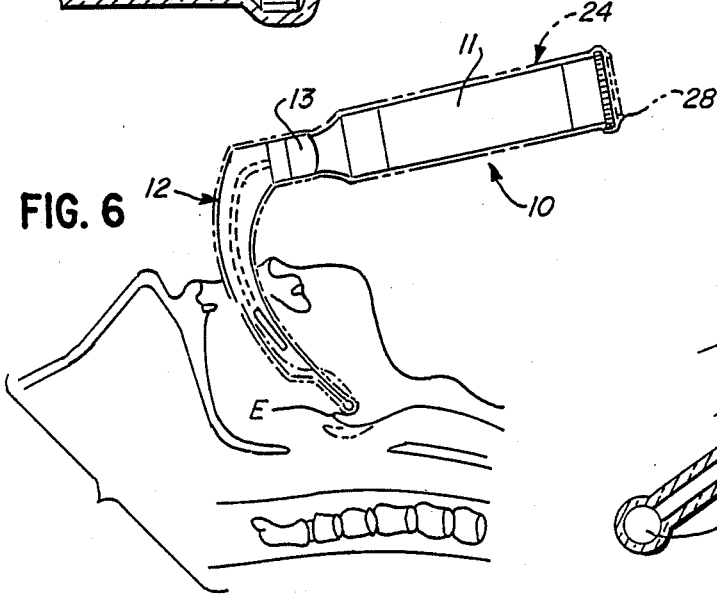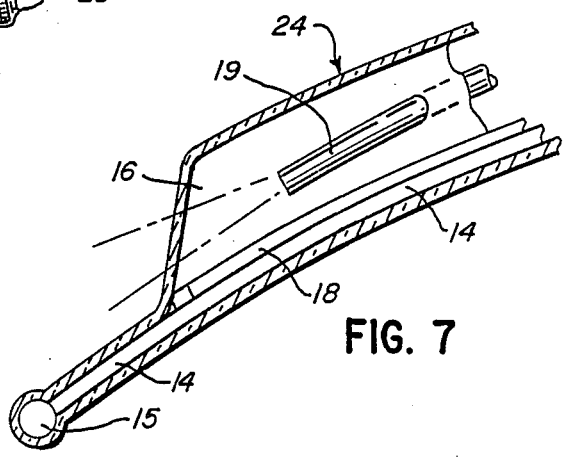

LARYNGOSCOPE ASSEMBLY INCLUDING DISPOSABLE PROTECTIVE ENCLOSURE

BACKGROUND OF THE INVENTION

The present invention relates to the field of laryngoscopes and, more specifically, to a laryngoscope assembly including a protective enclosure designed to preclude the possibility of transmitting a viral or bacterial infection from the instrument to the patient.

A laryngoscope is a hand held medical instrument used for visual examination of the larynx and trachea of a patient. It has a related use which is to facilitate the insertion of an endotracheal tube through the glottis and into the trachea for general anaesthesia during surgery. The procedure is referred to as endotracheal intubation.

The laryngoscope was invented in or about 1855 by Manual Garcia and introduced into medical practice in 1858 by Viennese surgeons Ludwig Turck and Johann Czermak. The instrument appears in two basic forms, an indirect laryngoscope and a direct laryngoscope. The former utilizes a mirror held near the back of the pharynx while a light is directed upon it from a reflector worn on the forehead of the examiner. The second type, a direct laryngoscope, is equipped with a built in illuminating device and a blade which moves the epiglottis and tongue forward to provide an unobstructed view of the larynx and the trachea. This application is concerned primarily with the second, or direct, type instrument.

The direct laryngoscope typically consists of a handle, a blade, and a connector fitting which holds the two together. The fitting is designed to permit quick attachment and detachment between the blade and the handle. A battery or batteries within the handle serve to power a light source. The latter may be a small incandescent lamp situated in the connector fitting or the upper portion of the handle. The lamp may be associated with a fiberoptic light conductor extending along the blade to a point located rearwardly of the tip portion of the blade. In certain older instruments, the incandescent lamp is mounted on the blade slightly to the rear of the tip portion and connected by wire to the battery in the handle.

Under current medical practices, instruments such as laryngoscopes should be sterilized after each usage to avoid the transmission of infection from one patient to another. Unfortunately, this precaution is not always followed with adequate thoroughness. Due to the construction of these instruments, particularly irregular sections of the blade and the connector fitting, there remains a residual risk of the presence of bacterial or viral infection sources in those areas and resulting transmission of infection from patient to patient.

U.S. Pat. No. 4,570,614 to Bauman discloses a laryngoscope with a disposable blade made partially of plastic material to avoid damage to the patient's upper front teeth from improper handling of the instrument. The patent also refers to a copending application disclosing a laryngoscope blade and disposable cover. The same inventor has also taken out three design patents showing three different configurations of disposable cover for specific laryngoscope blades. The design patents are Des. 242,396; Des. 242,397; and Des. 242,398. All of these disposable covers, as understood, cover the blade only and are open at the rear, risking exposure of the patient to possible contamination from the connector fitting and/or the handle due to inadequate sterilization.

SUMMARY OF THE INVENTION

The general object of the present invention is to provide a laryngoscope assembly including a disposable, fluid impervious, elastic safety enclosure which will positively protect the patient against contamination, not only from the blade, but also from the connector fitting and the handle.

Another object of the invention is to provide a laryngoscope assembly including a disposable, fluid impervious, elastic, protective safety enclosure of the foregoing character with means for retaining same in place on the instrument during use in examination and/or endotracheal intubation.

A further object of the invention is to provide a disposable protective safety enclosure of the type set forth above for a laryngoscope and adapted to transmit light effectively therethrough into the larynx and tracheal areas during examination and intubation.

Still another object of the invention is to provide an impervious elastic safety enclosure of the foregoing character having sufficient flexibility to accommodate a variety of laryngoscopes and blades.

BRIEF DESCRIPTION OF THE DRAWING FIGURES

FIG. 1 is a side elevational view of the disposable protective sanitary enclosure prior to surrounding the laryngoscope during its use in examination of a patient.

FIG. 2 is an end view of the disposable protective sanitary enclosure referred to above taken from its closed end.

FIG. 3 is a side elevational view of a common form of direct laryngoscope widely used for larynx and tracheal examination and to facilitate insertion of an endotracheal tube.

FIG. 4 is a top view of the laryngoscope shown in FIG. 3.

FIG. 5 is a side elevational view of the laryngoscope shown in FIG. 3 but which is encased in the protective sanitary enclosure shown in FIGS. 1 and 2.

FIG. 6 is a diagrammatic view of the sanitarily protected laryngoscope of FIG. 5 in use during examination of a patient's larynx and trachea prior to insertion of an endotracheal tube.

FIG. 7 is an enlarged fragmentary view showing the projecting end portion of the laryngoscope blade encased in the protective sanitary enclosure prior to examination of the patient.

FIG. 8 is an enlarged fragmentary view of the laryngoscope handle illustrating the manner in which the safety enclosure is retained on the handle against the bottom end cap.

While the present invention is susceptible of various modifications and alternative constructions, there is no intention to limit the invention to the specific form illustrated and described herein. On the contrary, the intention is to cover all modifications and alternative constructions falling within the spirit and scope of the invention as set forth in the appended claims.

DETAILED DESCRIPTION OF THE INVENTION

Referring more specifically to the drawing, the invention is there exemplified in connection with a typical direct laryngoscope 10 having a generally L-shaped configuration (FIGS. 3, 4). The instrument 10 comprises a handle 11, a somewhat arcuate shaped blade 12, and a connector fitting 13. The latter may be of the rigid interlocking type, or it may provide for angular adjustment of the blade relative to the handle. In the case of either construction, the instrument utilizes interfitting recesses, tongues and some type of locking mechanism (not detailed).

The arcuate blade 12 has a relatively straight outer end portion 14 terminating in a relatively small, transverse cylindrical tip 15 adapted to fit into the recess between the epiglottis E and the lower portion of the throat adjacent the base of the tongue. Starting at one side just beyond the outer end portion 14, is an upstanding abutment 16 adapted to deflect the tongue to avoid obstruction of the examiner's view of the larynx and trachea. The rearward portion of the abutment 16 has a tapered overhanging flange 17 which cooperates with the abutment in deflecting the tongue. On the opposite side of the abutment, at its lower edge, the abutment 16 has a flange 18 attaching it to the blade 12.

The blade 12 is equipped with a light source a short distance to the rear of the outer end portion 14. The source in the present instance comprises a fiberoptic bundle 19 having its outer end lodged in an oblong opening in the abutment 16 (FIGS. 3, 5, 7). The fiberoptic bundle extends rearwardly into the connector fitting 13 to a small incandescent lamp 20 powered by batteries 21 in the handle. The batteries are held in place in the handle by spring 29 and stops 30. The lamp 20 is controlled by an adjacent switch 22 also located in the connector fitting. The switch 22 is actuated to energize the lamp 20 when the blade 12 is inserted into the connector fitting and locked into place. The fiberoptic bundle 19 picks up the light from the lamp 20 and transmits it as cool light for illuminating the larynx and trachea area through a disposable, impervious, elastic safety enclosure 24 preferably formed from latex.

Turning next to the disposable, impervious, elastic safety enclosure 24 mentioned above, it will be noted that the device in the present instance comprises a first section 25 of generally oval cross section closed at one end. The section 25 has appropriate size when stretched lengthwise to envelop the outer end portion 14 of the blade 12. The enclosure 24 also comprises a second section 26 of generally round cross section and greater cross-sectional area than the first section 25. The second section 26 has sufficient length when stretched longitudinally to envelop the remaining portion of the blade 12 and a portion of the connector fitting 13. The enclosure 24 further includes a third section 27 of generally round cross section with greater diameter than section 26, and length sufficient to cover to the full length of the handle 11 plus a small annular overlap 31 at its outer end. The annular overlap 31 of the section 27 is formed with a relatively heavy elastic bead 28 which tends to hold the overlapping end of section 27 in place against the bottom cap 23 of the handle 11. The diameter and length of all three sections of the safety enclosure 24 is such that they tend to stretch longitudinally and diametrically to conform substantially to the shape of the major components of the laryngoscope (FIGS. 3, 5).

The safety enclosure 24 may conveniently be supplied in compact form wherein it is rolled upon itself. It may then be installed readily upon the laryngoscope 10 by fitting it upon the outer end portion 14 of the blade and unrolling it over the remaining portions of the instrument.

The instrument 10 with the safety enclosure 24 thereon may be used in the traditional way by inserting the outer end portion of the blade into the recess between the epiglottis and the forward area of the throat and tongue. The instrument is then drawn forward, avoiding any pivoting on the upper front teeth, to expose the larynx and trachea for examination and, where necessary, for endotracheal intubation. Upon withdrawal of the instrument 10, the safety enclosure 24 may be removed by rolling it back upon itself. This helps prevent exposure of the patient's oral secretions to the operator of the laryngoscope. The blade 10 may then be unlocked and removed from the connector fitting 13, deenergizing the lamp 20 in the process.

We claim as our invention:

1. In a laryngoscope assembly, the combination comprising
   (a) a laryngoscope handle;
   (b) a laryngoscope blade;
   (c) a connector fitting attaching said blade to said handle;
   (d) a light source mounted on said blade and powered from battery means in said handle;
   (e) a disposable, fluid impervious, elastic safety enclosure adapted to be stretched longitudinally and diametrically over said blade, said connector fitting, and said handle;
   (f) said safety enclosure being sufficiently light permeable to permit illumination of the larynx and trachea during use of said laryngoscope assembly; and
   (g) said safety enclosure having an annular extension overlapping the bottom cap of said handle and terminating in an elastic bead of substantially smaller diameter than said handle to retain said safety enclosure in place on said handle.

2. A laryngoscope assembly as defined in claim 1, wherein said light source comprises a fiberoptic conductor powered from a lamp in said connector fitting and adapted to project cool light through said safety enclosure.

3. A laryngoscope assembly as defined in claim 1, wherein said safety enclosure is formed with a first section having a closed end adapted to envelop the outer end portion of the blade; a second section of a greater cross-sectional area than said first section and adapted to envelope the remaining portion of said blade and a portion of said connector fitting; and a third section of a greater cross-sectional area than said second section adapted to cover the full length of said handle; and said safety enclosure being made from latex.

4. The combination of a laryngoscope assembly having a handle, a blade, and a connector fitting therebetween, with a disposable, fluid impervious, elastic safety enclosure, said combination comprising:
   (a) a first section of said elastic safety enclosure having a closed end and adopted to envelope the outer end portion of said blade;
   (b) a second section of said safety enclosure having a greater cross-sectional area than said first section and adapted to envelope the remaining portion of said blade and said connector fitting;
   (c) a third section of said safety enclosure having a greater cross-sectional area than said second section and adapted to cover the gripping area of said handle with an annular overlap at the end of said handle; and (d) a generally circular bead integral with said annular overlap having a cross sectional thickness substantially greater than the thickness of said safety enclosure.

5. A disposable, fluid impervious, elastic safety enclosure as defined in claim 4, wherein at least said first and second sections are substantially transparent and formed from latex.

6. A disposable, fluid impervious, elastic safety enclosure as defined in claim 4, wherein said safety enclosure is initially supplied in compact form rolled upon itself, and subsequently unrolled and stretched longitudinally and diametrically over said instrument and an annular area on the outer face of the bottom cap of said handle.

7. A disposable, fluid impervious, elastic safety enclosure as defined in claim 4, wherein said safety enclosure has a thickness of at least 6 mils and an open end portion surrounded by a bead of smaller diameter than said handle, said bead having a cross sectional thickness substantially greater than 6 mills.

8. A disposable, fluid impervious, elastic safety enclosure as defined in claim 5, wherein said safety enclosure has a thickness of approximately 6 mils.

* * * * *